United States Patent
Stelzer

(10) Patent No.: US 6,215,022 B1
(45) Date of Patent: Apr. 10, 2001

(54) METHOD FOR PRODUCING 3-HYDROXY-2-METHYLBENZOIC ACID

(75) Inventor: Uwe Stelzer, Burscheid (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/462,047

(22) PCT Filed: Jul. 6, 1998

(86) PCT No.: PCT/EP98/04159

§ 371 Date: Dec. 30, 1999

§ 102(e) Date: Dec. 30, 1999

(87) PCT Pub. No.: WO99/03814

PCT Pub. Date: Jan. 28, 1999

(30) Foreign Application Priority Data

Jul. 18, 1997 (DE) .............................................. 197 30 848

(51) Int. Cl.⁷ ..................................................... C07C 65/01

(52) U.S. Cl. ............................................................. 562/475
(58) Field of Search ............................................... 562/475

(56) References Cited

U.S. PATENT DOCUMENTS 5,530,028    6/1996    Lidert et al. .

OTHER PUBLICATIONS

J. Chem. Soc., (Month unavailable) 1909, pp. 1883 to 1889, Baudisch et al, The Reduction of of 6–Hydroxy–o–toluic Acid.
Amer. Chem. Soc. vol., 58, May 1936, pp. 749 to 753, Fieser et al, The Structure of Anthracene.

*Primary Examiner*—Paul J. Killos
(74) *Attorney, Agent, or Firm*—Joseph C. Gil; Diderico van Eyl

(57) ABSTRACT

The invention relates to a novel method for preparing 3-hydroxy-2-methylbenzoic acid by reacting disodium 3-amino-1,5-naphthalinedisulfonic acid with aqueous potassium hydroxide solution at a pressure of at least 100 bar.

1 Claim, No Drawings

METHOD FOR PRODUCING 3-HYDROXY-2-METHYLBENZOIC ACID

The present invention relates to a novel process for preparing 3-hydroxy-2-methylbenzoic acid.

It is known that 3-hydroxy-2-methylbenzoic acid is obtained by reacting sodium 2-naphthylamine-4,8-disulfonate with 50% strength NaOH at from 250 to 260° C. However, the yield is only about 10% (J. Chem. Soc. 95, 1883 (1909), see also J. Amer. Chem. Soc. 58, 749 (1936)). J. Chem. Soc. 2773 (1961) describes an improved yield of 76% when an initial pressure of 40 bar of nitrogen is used. However, the product obtained by this process is heavily contaminated; the actual yield is therefore significantly lower.

It was the object of the present invention to provide an improved, simple and industrially feasible process for preparing 3-hydroxy-2-methylbenzoic acid.

The present invention provides a process for preparing 3-hydroxy-2methylbenzoic acid of the formula (I)

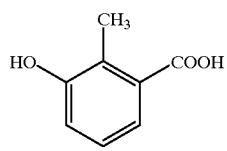

(I)

which comprises reacting disodium 3-amino-1,5-naphthalenedisulfonic acid of the formula (II)

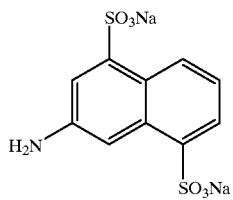

(II)

with 10 to 20 equivalents of potassium hydroxide and less than 55% by weight of water, based on the amount of potassium hydroxide, at temperatures from 250 to 300° C. and under a pressure of at least 100 bar.

Surprisingly, the process according to the invention results in higher yields of 3-hydroxy-2-methylbenzoic acid than the known processes. In addition, the product is obtained in such a high purity that it can be used without any further purification for further reactions.

The process according to the invention can be represented by the following formula scheme:

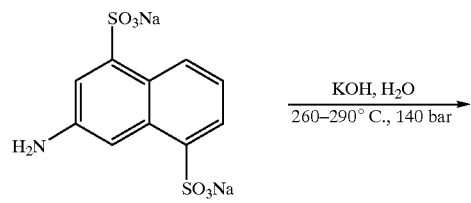

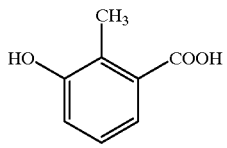

In general, 10 to 20 equivalents of potassium hydroxide, preferably 14 to 18, particularly preferably 15 equivalents, are used, based on the disulfonic acid of the formula (I) employed.

The amount of water used is generally less than 55% by weight, based on the amount of KOH, and preference is given to using from 15 to 50% by weight of water.

The reaction temperature is generally from 250 to 300° C., preferably from 260 to 290° C.

The reaction pressure is generally between 30 and 160 bar.

The reaction pressure is preferably at least 100 bar, preferably between 100 and 160 bar.

In general, the process according to the invention is carried out by initially charging the compound of the formula (I) in an autoclave with KOH and water, and applying the desired pressure (for example 40 bar) using nitrogen. The mixture is then heated to the reaction temperature, resulting in a reaction pressure of preferably at least 100 bar.

Work-up is generally carried out such that the reaction mixture is washed out of the autoclave using water and adjusted to an approximately neutral pH using an acid (preferably an inorganic acid, such as hydrochloric acid).

The mixture is then treated with montmorillonite, kieselguhr (for example (Celite®), activated carbon (for example Norite®), bleaching earth (for example Tonsil®) or bone charcoal, stirred and filtered. The mixture is then extracted with an organic solvent (for example methyl acetate, ethyl acetate, methylene chloride or diethyl ether) and the aqueous phase is adjusted to a pH between 1 and 4, preferably 2 and 3, using an acid (cf. above). The aqueous phase is then reextracted (cf. above), and the reaction product is isolated from the combined organic phases in a customary manner (compare also the working example).

3-Hydroxy-2-methylbenzoic acid is an important intermediate for the synthesis of insecticidally active compounds (see, for example, EP-A-0 602 794, EP-A-0 639 559).

EXAMPLE 1

160 g (0.33 mol, 71%) of 3-amino-1,5-naphthalenedisulfonic acid disodium salt are initially charged with 250 ml of $H_2O$ and 330 g of KOH (5 mol, 85%) in an autoclave, and a pressure of 40 bar is applied using $N_2$. The mixture is heated at 280° C. for 8 hours. The pressure increases to 143 bar. After cooling and venting of the autoclave, the black-brown suspension is washed out of the autoclave using water. With cooling, the pH is adjusted to 7.2 using concentrated HCl, and the mixture is admixed with Celite® 15 to 20 g, stirred and filtered. The aqueous phase is extracted with ethyl acetate (2×150 ml) and subsequently adjusted to pH 2 to 3 using concentrated HCl. The aqueous phase is then reextracted with ethyl acetate (3×150 ml), the combined organic phases are dried and the solvent is removed under reduced pressure. This gives 40.9 g, 81.6% of the desired, almost colorless solid. Melting point: 142 to 143° C.

EXAMPLE 2

Comparative Example, cf J. Chem. Soc. 2773 (1961)

164 g (70% disodium 3-amino-1,5-naphthalenedisulfoic acid are, with 200 ml of $H_2O$ and 200 g of NaOH and an initial $N_2$ pressure of 40 bar, heated in an autoclave at 280° C. for 12 hours. The residue, which smells of ammonia, is dissolved in 1.5 liters of ice-water and, with cooling, acidified with concentrated HCl. Upon acidification, the mixture foams. The aqueous phase is extracted repeatedly with ethyl acetate, the combined organic phases are dried and the solvent is removed under reduced pressure. 34.7 g of a gray solid which, according to GC, contains 77.6% of the desired product are isolated. From this, the yield can be calculated to be 54% of theory.

What is claimed is:

1. A process for preparing 3-hydroxy-2-methylbenzoic acid of the formula (I)

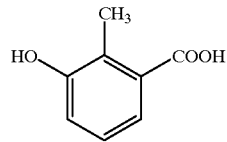

which comprises reacting disodium 3-amino-1,5-naphthalenedisulfonic acid of the formula (II)

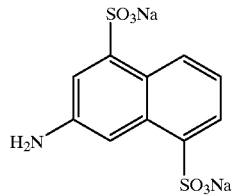

with 10 to 20 equivalents of potassium hydroxide and less than 55% by weight of water, based on the amount of potassium hydroxide, at temperatures from 250 to 300° C. and under a pressure of at least 100 bar.

* * * * *